United States Patent [19]

Roy et al.

[11] Patent Number: 5,112,858
[45] Date of Patent: May 12, 1992

[54] ANTIBIOTIC, ARANOROSIN, A MICROBIOLOGICAL PROCESS FOR THE PREPARATION THEREOF, AND THE USE THEREOF AS A PHARMACEUTICAL

[75] Inventors: Kirity Roy; Triptikumar Mukhopadhyay; Goukanapalli C. S. Reddy; Erra K. S. Vijayakumar; Bimal N. Ganguli, all of Bombay, India; Richard H. Rupp, Königstein/Taunus, Fed. Rep. of Germany; Hans-Wolfram Fehlhaber, Idstein/Taunus, Fed. Rep. of Germany; Herbert Kogler, Kelkheim, Fed. Rep. of Germany

[73] Assignee: Hoechst Aktiengesellschaft, Frankfurt, Fed. Rep. of Germany

[21] Appl. No.: 350,288

[22] Filed: May 11, 1989

[30] Foreign Application Priority Data

May 13, 1988 [DE] Fed. Rep. of Germany ....... 3816411

[51] Int. Cl.⁵ .................. A61K 31/335; C07D 311/96
[52] U.S. Cl. ..................................... 514/462; 549/331
[58] Field of Search ......................... 549/531; 514/462

[56] References Cited
U.S. PATENT DOCUMENTS

| | | | |
|---|---|---|---|
| 4,174,327 | 11/1979 | Renold et al. | 549/331 |
| 4,190,591 | 2/1980 | Kaiser et al. | 549/331 |
| 4,588,591 | 5/1986 | Kaplan et al. | 549/331 |

OTHER PUBLICATIONS

Fehlhaber et al., "J.A.C.S.", vol. 110, 1988, pp. 8242-8244.
G. Orr et al., Mycologia, vol. 69, pp. 126-163 (1977).
G. Ainsworth et al., The Fungi, An Advanced Treatise, vols. IVA & IVB (Table of Contents) (1973).

Primary Examiner—C. Warren Ivy
Assistant Examiner—Celia Chang
Attorney, Agent, or Firm—Finnegan, Henderson, Farabow, Garrett and Dunner

[57] ABSTRACT

A new antibiotic, aranorosin, a microbiological process for the preparation thereof, and the use thereof as a pharmaceutical.

Aranorosin, a compound of the formula

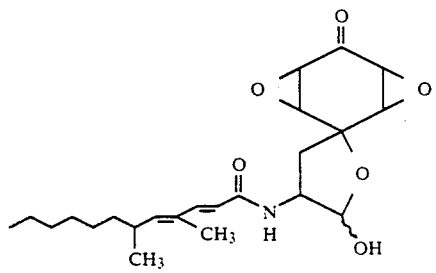

can be prepared with the aid of the fungus culture Y-30499 (DSM 4151). Aranorosin has an antibiotic action as well as an action against malignant tumors.

3 Claims, No Drawings

ANTIBIOTIC, ARANOROSIN, A MICROBIOLOGICAL PROCESS FOR THE PREPARATION THEREOF, AND THE USE THEREOF AS A PHARMACEUTICAL

DESCRIPTION

The present invention relates to a new antibiotic, aranorosin, and to a process for the preparation thereof from fungus culture No. Y-30499.

The fungus culture Y-30499 for the preparation of aranorosin was isolated from soil and identified as *Pseudoarachiniotus roseus* Kuehn (Mycologia 69; 126-163, 1977), which belongs to the family Gymnoascaceae, order Eurotiales, class Plectomycetes, subdivision Ascomycotina and division Eumycota (G. C. Ainsworth, F. K. Sparrow and A. S. Sussman (Editors) 1973, "The Fungi, An Advanced Treatise" Volume IVA and IVB, Academic Press, New York). No antibiotics produced by this fungus culture have been described in the literature.

The culture Y-30499 was deposited on June 23, 1987, at the Deutsche Sammlung von Mikroorganismen (German Microorganism Collection), Göttingen, under receipt number DSM 4151.

Aranorosin has the following structural formula

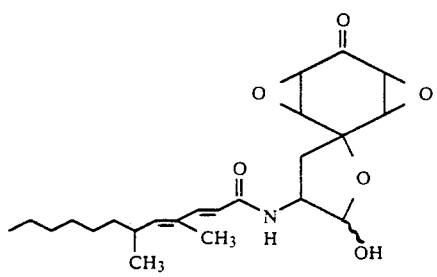

The present invention also relates to a process for the preparation of the new antibiotic aranorosin from the fungus culture No. Y-30499, which comprises this fungus culture being cultivated by fermentation under aerobic conditions on a nutrient medium which contains carbon sources, nitrogen sources, inorganic nutrient salts and trace elements, at a temperature between 24° and 30° C. and at a pH between 6.0 and 8.0, for 66 to 90 hours, and the antibiotic being isolated and purified by the customary methods from the culture broth.

Suitable carbon sources are glucose, sucrose, starch or dextrin. Starch is preferred as carbon source. Suitable nitrogen sources are soybean meal, tryptone, yeast extract, beef extract, malt extract, corn steep liquor, peptone or inorganic substances such as ammonium salts. The preferred nitrogen source is soybean meal. The inorganic nutrient salts can be sodium chloride, potassium hydrogen and dihydrogen phosphate, or calcium carbonate. Trace elements which can be present are salts of iron, managenese, copper, zinc or cobalt.

The culture No. Y-30499 is expediently cultivated at 26° C. (±1° C.) and pH 6.5. The cultivation can be carried out both in shaken flasks and in fermenters. The cultivation is preferably carried out for 72 hours. The maximum yield of the antibiotic according to the invention is evidently obtained after this time. Submerged cultivation is possible and preferred. If this fungus culture is cultivated in fermenters, this can take place in the presence of an antifoam agent such as a linear polyether based on propylene oxide with a mean molecular weight of 2,000±100 (Desmophen ® from Bayer AG).

The progress of the formation of the aranorosin according to the invention can be detected by measuring the bioactivity of the culture broth against *Bacillus subtilis* and *Aspergillus niger* by the known agar plate diffusion determination method.

The aranorosin according to the invention is isolated and purified by known standard laboratory methods from the culture broth. For example, the culture is centrifuged to separate mycelium from the culture filtrate. The aranorosin can be obtained from the culture filtrate by extraction using a solvent which is immiscible with water, such as ethyl acetate, chloroform or butanol, after the pH of the filtrate has been adjusted to 7.0; ethyl acetate is preferred as extractant in this connection. Aranorosin in the mycelium is obtained by extracting the mycelium with a solvent such as ethyl acetate, chloroform, methanol, ethanol, acetone or butanol, the preferred solvent being acetone. After the extraction, the solvent is removed by evaporation in vacuo, and the aqueous layer is diluted with water and extracted again with a solvent such as the abovementioned. The solvent extract from both the culture filtrate and the mycelium are combined, evaporated to dryness and purified using, for example, column chromatography.

EXAMPLE 1

Maintenance of the Type Culture No. Y-30499

The culture No. Y-30499 is maintained on Sabouraud's glucose/agar medium of the following composition:

| | |
|---|---|
| Glucose | 40 g |
| Peptone | 10 g |
| $Na_2HPO_4$ | 1 g |
| Agar | 15 g |
| Distilled water | 1 l |
| pH | 6.5 |

After the ingredients have been completely dissolved by heating, the medium is distributed among test tubes and then sterilized at 121° C. for 20 minutes. The pH before autoclaving is 6.5. The test tubes are cooled in an inclined position to prepare agar slants. The agar slants are inoculated with spores of the culture No. Y-30499 isolated from soil, and incubated at 26° C. (±1° C.) until satisfactory sporulation is observed. The cultures with satisfactory sporulation are stored in a refrigerator.

Cultivation of the culture No. Y-30499 in shaken flasks for the preparation of the new antibiotic aranorosin by fermentation.

Composition of the seed culture medium:

| | |
|---|---|
| Soluble starch | 15 g |
| Soybean meal | 15 g |
| Glucose | 5 g |
| $CaCO_3$ | 2 g |
| NaCl | 5 g |
| Yeast extract | 2 g |
| Corn steep liquor | 1 g |
| Distilled water | 1 l |

100 ml samples of the above seed culture medium are distributed among wide-necked 500 ml Erlenmeyer flasks and sterilized at 121° C. for 20 minutes. The pH is adjusted to 6.5 before autoclaving and is 6.0 thereafter. The flasks are cooled and then inoculated with a few platinum loops full of the abovementioned culture with satisfactory sporulation, and shaken at 240 rpm and 26° C. (±1° C.) for 60 hours, during which satisfactory growth is observed. The seed culture obtained in this way is used to inoculate the production medium of the following composition:

Composition of the production medium:

| Soybean meal | 20 g |
|---|---|
| Glucose | 30 g |
| CaCO$_3$ | 6 g |
| NaCl | 3 g |
| NH$_4$Cl | 1.5 g |
| KH$_2$PO$_4$ | 2 g |
| ZnSO$_4$.7H$_2$O | 0.22 mg |
| CaCl$_2$ | 0.55 mg |
| MnCl$_2$.4H$_2$O | 0.5 mg |
| FeSO$_4$.7H$_2$O | 0.5 mg |
| CuSO$_4$.5H$_2$O | 0.16 mg |
| CoCl$_2$.6H$_2$O | 0.16 mg |
| Distilled water | 1 l |

200 ml samples of the above production medium are distributed among 1 liter Erlenmeyer flasks and sterilized at 121° C. for 20 minutes. The pH of the medium is adjusted to 6.5 before autoclaving and is 6.0 thereafter. The flasks are cooled and then inoculated with the above seed culture medium (1% V/V). The fermentation is carried out in a rotary shaker at 26° C. (±1° C.) for 72 hours. Aranorosin production is tested by the profile of activity against *Bacillus subtilis* and *Aspergillus niger*. After harvesting, the culture broth is centrifuged, and the aranorosin is isolated from both the mycelium and the culture filtrate and purified as described below.

Isolation and Purification of Aranorosin

The culture filtrate (143 liters, obtained by centrifugation of about 150 liters of culture broth) is extracted at pH 6.7 with 50 liters of ethyl acetate. The extraction is repeated again, and the combined extracts are freed of ethyl acetate and concentrated under reduced pressure at 35° C. The cake of mycelium (11.3 kg, obtained by centrifugation of about 150 liters of culture) is extracted twice with 30 liters of acetone each time in a similar manner. Most of the acetone is removed from the combined extracts under reduced pressure at 35° C., and the remaining aqueous phase is extracted twice with 3 liters of ethyl acetate each time. The ethyl acetate extracts are concentrated under reduced pressure at 35° C. and combined with the concentrate of the culture filtrate extract.

The reddish brown crude antibiotic aranorosin (196 g) is chromatographed on silica gel (2 kg, 100–200 openings per inch) and eluted with chloroform/methanol mixtures with increasing methanol contents until the methanol concentration in the chloroform reaches 5%. The aranorosin is eluted with between 2 and 4% methanol in the chloroform.

The semipure aranorosin (68 g) is again chromatographed on silica gel (1.3 kg, 200–300 openings per inch) and eluted with a chloroform/methanol mixture as mentioned above for the first column chromatography, resulting in further purified aranorosin (13 g).

This product is chromatographed in turn on silica gel (650 g, 200–300 openings per inch) using a benzene/acetonitrile mixture (7:3) as eluent. Pure aranorosin (4.1 g) is isolated from this as a white solid.

The latter is dissolved in ethyl acetate and precipitated with hexane to remove traces of pigment.

EXAMPLE 2

Cultivation of the Culture No. Y-30499 in Fermenters for the Preparation of the New Antibiotic Aranorosin by Fermentation Stage I: Preparation of the Seed Culture a) In shaken flask The seed culture medium from Example 1 (100 ml) is placed, at a pH previously adjusted to 6.5, in previously sterilized wide-necked 500 ml Erlenmeyer flasks, sterilized at 121° C. in an autoclave for 20 minutes, cooled and inoculated with a few platinum loops full of the culture from Example 1 with satisfactory sporulation. The pH after sterilization is 6.0. The flasks are incubated in a rotary shaker at 240 rpm and 26° C. (±1° C.) for 72 hours.

b) In Suction Flasks:

One liter of the seed culture medium from Example 1 is placed in a 5 liter suction flask, sterilized at 121° C. in an autoclave for 30 minutes, cooled and inoculated with a few platinum loops full of the culture from Example 1 with satisfactory sporulation. The pH of the medium is 6.5 before sterilization and 6.0 thereafter. The flasks are placed in a rotary shaker and incubated at 26° C. (±1° C.) and 240 rpm for 72 hours.

Stage II: Fermentation a) On a Small Scale

Ten liters of the production medium from Example 1 are autoclaved with 0.04% Desmophen ® in a 15 liter stainless steel fermenter at 121°–122° C. for 36 minutes. The pH is 6.5 before sterilization and 6.0 thereafter. Twenty liters of the production medium from Example 1 containing 0.04% "Desmophen ®" are placed in 30 liter stainless steel fermenter and sterilized therein at 122° C. under a steam pressure of 1.2 kg/cm$^2$ for 32 minutes. The pH is adjusted to 6.5 before sterilization and is 6.0 thereafter. After cooling, the fermenter is inoculated with 1–3% (V/V) of the seed culture under aseptic conditions and is operated at 26° C. (±1° C.), stirring at 120–180 rpm depending on the growth and foaming, and with aeration with 6–10 liters per minute.

b) On a Large Scale

One hundred liters of the production medium from Example 1 with the pH adjusted to 6.5 and 0.04% Desmophen ® are placed in a previously sterilized 150 liter fermenter. The production medium is sterilized therein at 121°–122° C. under a steam pressure of 1.2 kg/cm$^2$ for 32 minutes. The pH thereafter is 6.0. After the fermenter has been cooled to 26° C. it is inoculated with 1% (V/V) of the seed culture under aseptic conditions and operated at a temperature of 26° C. (±1° C.), stirring at 100 rpm and aerating with 60 liters per minute.

Aranorosin production is tested by the profile of activity against *Bacillus subtilis* and *Aspergillus niger*. The fermenter is harvested after 72 hours. The culture broth is centrifuged to remove the mycelium from the culture filtrate and both are then worked up as described in Example 1.

The aranorosin was examined by chemical analysis and spectroscopic methods. It has the following properties:

Physical properties of the antibiotic aranorosin

| | |
|---|---|
| 1. Appearance | White solid |
| 2. Molecular formula | $C_{23}H_{3}NO_{6}$ |
| 3. Molecular weight | 419 |
| 4. Melting point | 150° C. (decomposition) |
| 5. $[\alpha]_D^{25}$ | −2.42° (c = 2.58 in chloroform) |
| 6. Rf (thin-layer chromatography on precoated silica gel plates) | 0.42 (85:15 chloroform: methanol, 0.39 (6:4 benzene: acetonitrile) 0.49 (ethyl acetate) |
| 7. Elemental analysis | C 64.75; H 7.83; N 3.16% |
| 8. Solubility | Insoluble in petroleum ether and water; sparingly soluble in benzene; soluble in diethyl ether, chloroform, acetone, ethyl acetate, dimethyl sulfoxide and methanol. |

Spectral data for the new antibiotic aranorosin
UV (Methanol): λ max 264 nm

Spectral data for the new antibiotic aranorosin
IR (KBr), Principal υ max. in cm$^{-1}$: 3448 (—OH and —NH), 1710 (6-membered ring ketone), 1653 (sec. amide carbonyl, band I), 1538 (sec. amide carbonyl, band II), 1242 (epoxide), 980 (transdisubstituted alkene) and 844 (trisubstituted alkene)

$^1$H NMR: (270 MHz, CDCl$_3$, δ in ppm with TMS as reference) 0.86 t, J-6 Hz, —CH$_3$), 0.95 (d, J=7 Hz ), 1.24 (s broad, 5X—CH$_2$), 1.75 (d, J=0.5 Hz=CHCH$_3$), 2.03 (dd, J=12.5, 10.5 Hz, COCHH), 2.48 (m, =CHCH), 2.60 (dd, J=12.5, 8.5 Hz COCHH), 3.43 (m,CH—O—CH), 3.55 (dd, J=3.5, 3.5 Hz, O—CH), 3.66 (dd, J=3.5 Hz, O—CH), 4.26 (s broad, 1H, D$_2$O, exchangeable), 4.77 (m, NHCH), 5.61 (d, J=4.5 Hz, CHOH), 5.65 (dd, J=10, 0.5 Hz, =CH), 5.74 (d, J=15 Hz, =CH), 6.06 (d, J=8 Hz, —NH) and 7.23 (d, J=15 Hz, =CH).

$^{13}$C NMR: (67.8 MHz CDCl$_3$ δ in ppm with TMS as reference)

Spectral data for the new antibiotic aranorosin —C-NMR: 12.47 (q), 14.05 (q), 20.49 (q), 22.60 (t), 27.44 (t), 29.38 (t), 31.81 (t), 33.20 (d), 35.96 (t), 37.23 (t), 52.00 (d), 55.54 (d), 55.78 (d), 62.85 (d), 64.21 (d), 78.92 (s), 96.53 (d), 116.85 (d), 130,72 (s), 147.33 (d), 148.40 (d), 166.67 (s) and 198.19 (s).

The new compound aranorosin has bactericidal and fungicidal properties. The minimum inhibitory concentrations of the new antibiotic aranorosin required to inhibit various strains of bacteria and fungi are listed in Table I.

TABLE I

| Test organisms | Minimum inhibitory concentration (MIC) of the new antibiotic aranorosin in μg/ml |
|---|---|
| Staphylococcus aureus 209 P | 1.5 |
| Staphylococcus aureus 20204 | 1.5 |
| Staphylococcus aureus R 85 | 1.5 |
| Staphylococcus aureus SG 511 | 0.78 |
| Staphylococcus aureus 285 | 0.78 |
| Staphylococcus aureus 503 | 0.78 |
| Streptococcus faecalis | 3.0 |
| Streptococcus pyogenes 308A | 0.78 |
| Streptococcus pyogenes 77 A | 0.78 |
| Bacillus subtilis | 1.5 |
| Sarcina lutea | 1.5 |
| Pseudomonas aeruginosa ATCC 9027 | >100 |
| Pseudomonas aeruginosa 1592 E | >100 |
| Pseudomonas aeruginosa 1771 | >100 |
| Pseudomonas aeruginosa 1771 M | 50 |
| E. coli Ese 2231 | >200 |
| E. coli 055 | 100 |
| E. coli TEM | 100 |
| E. coli 1507 E | 100 |
| E. coli DC O | 100 |
| E. coli DC 2 | 25 |
| Salmonella typhimurium | 50 |
| Klebsiella aerogenes 1082 E | 50 |
| Klebsiella aerogenes 1522 E | 100 |
| Enterobacter cloacae P 99 | 100 |
| Enterobacter cloacae 1321 E | 100 |
| Candida albicans | 30 |
| Saccaromyces cerevisiae | 500 |
| Aspergillus niger | 7.5 |
| Penicillium italicum | 30 |
| Cercospora beticola | 3.0 |
| Botrytis cinerea | 30 |
| Microspora gypseum | 3.0 |

Aranorosin is thus effective against Gram-positive and Gram-negative bacteria as well as yeasts and filamentous fungi and can be used as an antibiotic for the treatment of bacterial and fungal infections.

Aranorosin likewise has cytostatic properties and is therefore suitable as a pharmaceutical for the treatment of oncoses, for example for controlling malignant tumors and leukemias.

We claim:
1. A compound of the formula

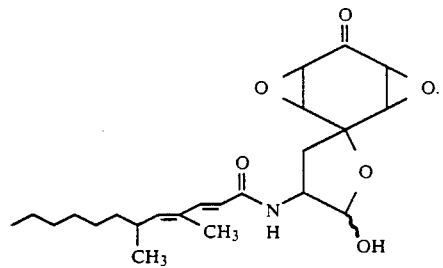

2. A pharmaceutical which contains a compound as claimed in claim 1 in addition to pharmaceutically acceptable carriers or diluents.

3. A method of alleviating a bacterial or fungal infection in a mammal, said method comprising administering to said mammal an amount of the compound of claim 1 effective to inhibit growth of said bacteria or fungi.

* * * * *